| United States Patent [19] | [11] Patent Number: 4,840,658 |
| Kakisawa et al. | [45] Date of Patent: Jun. 20, 1989 |

[54] ALGICIDAL COMPOSITION

[75] Inventors: Hiroshi Kakisawa; Takenori Kusumi, both of Ibaraki; Nobuo Ohno, Osaka, all of Japan

[73] Assignee: Sumitomo Chemical Company, Limited, Osaka, Japan

[21] Appl. No.: 25,694

[22] Filed: Mar. 13, 1987

[30] Foreign Application Priority Data

Mar. 14, 1986 [JP] Japan ................................. 61-57925

[51] Int. Cl.⁴ ............................................. A01N 37/06
[52] U.S. Cl. ........................................ 71/67; 71/113; 106/18; 43/7
[58] Field of Search ..................................... 71/67, 113

[56] References Cited

U.S. PATENT DOCUMENTS 4,398,937  8/1983  Van Aller et al. ..................... 71/67

FOREIGN PATENT DOCUMENTS 0121425   9/1975  Japan ..................................... 71/67
255706    5/1984  Japan ..................................... 71/67
143301   12/1984  Japan ..................................... 71/67

OTHER PUBLICATIONS

M. Matick, "South African Pilchard Oil", *Biochemical Journal,* 68, (1958), pp. 692-695.
F. Gunstone, "An Introduction to the Chemistry . . . Glycerides", *Chemistry and Biochemistry of Fatty Acids,* Chapman and Hall Ltd., p. 20.
Bull, Environ. Contam. Toxicol. 18 (3), 291 (1971).
J. Agr. Food Chem. 27 (1), 69 (1979).
Lewin, R., "Physiology and Biochemistry of Algae", *Academic Press,* 1962, pp. 592-541.
Markley, K. S., *Fatty Acids,* 2nd Edition, Part 5, Interscience Publ., 1968, pp. 3195-3197, 3245-3247, 3250-3253.
Findlay et al., "Antibacterial Constituents of, etc.", CA 102: 21,199m, 1985.
Matic et al., Biochemistry Journal, vol. 68, 695 (1958).

*Primary Examiner*—Glennon H. Hollrah
*Attorney, Agent, or Firm*—Sughrue, Mion, Zinn, Macpeak & Seas

[57]                ABSTRACT

An algicidal composition which is effective against red tide comprises, a higher fatty acid or its salt as an active ingredient, such as 6, 9, 12, 15-octadecatetraenic acid.

6 Claims, No Drawings

ALGICIDAL COMPOSITION

This invention relates to an algicidal composition. More particularly, it relates to an algicidal composition comprising higher fatty acid or salts thereof.

A composition containing germanium compound is suggested as an aquatic algae-controlling agent [Japanese publication (Kokai) No. 60-255706].

However, such composition is subjected to restriction in an amount to be applied and an embodiment of use from a view-point of contamination to aquatic environment. This is why exploitation of a new algicidal composition causes been desired which has little contamination to the environment and has much algicidal activity.

The present inventors studied biologically active substances in marine organisms and found strong algicidal activity of 6Z, 9Z, 12Z, 15Z-octadecatetraenoic acid against marine dinoflagellates (Dinophyceae), which is an unsaturated higher fatty acid isolated from an edible brown alga "Mozuku" (*Cladosiphon okumuranus*). They have further found at last growth inhibition activity as well as algicidal activity of the higher fatty acid and salts thereof against algae which do great harm to fish- and shellfish-aquaculture and against those including sea weeds which adhere to and damage artificial products in sea The higher fatty acid which is an active ingredient for the present composition is obtained, for example, by hydrolysis of fish oil and has 12-30, preferably 16-24 carbon atoms, from an economical point. The presence of C-C unsaturated bond is not necessary but preferable. More preferable is the presence of two or more unsaturated bonds conjugated or not conjugated in the molecule. Salts of the acid include alkali metal salts, alkaline earth metal salts, ammonium salts, organic quaternary ammonium salts and phosphonium salts Algae to which the present composition is applied are genuses: Haptophyceae, Cryptophyceae, Raphydophyceae, Bacillariophyceae, Chlorophyceae, Prasinophyceae, Euglenophyceae, Dinophyceae, Cyanophyceae, etc.

More specifically, mention may be made of the following species: *Cric-osphaera roscoffensis,* Cryptomonas sp., *Chattonella antiqua, Chattonella marina, Olisthodiscus luteus, Heterosigma akashiwo, Chaetoceros debile, Skeletonema costatum, Stephanopyris palmeriana,* Chlamydomonas sp., Oltmannsiella sp., *Hafniomonas reticulata,* Nephroselmis sp., *Pteosperma cristatum,* Pyramimonas sp., *tetraselmis cordiformis,* Eutreptia sp., *Gymnodinium nagasakiense, Gymnodinium sanguineum, Gymnodinium breve (Ptychodiscus brevis), Gonyaulax monilata, Gonyaulax excavata, Gonyaulax tamarensis, Gyrodinium aureolum, Prorocentrum mariae lelouriae, Noctiluca scintillans, Noctiluca miliaris, Pyrodinium bahamense var compressa, Gymnodinium catenatum, Cochlodinium cartenutum, Protogouyaulax catenella, Protogouyaulux tamavensis, Protogouyaulax acatenella , Cochlodinium catenatum, Microcystis aeruginosa, Aphanizomenon flos-aquae, Oscillatoria agordhii, Cyanodictyon imperfectum, Gonyaulax catenella, Gonyaulax polyedra, Gonyaulax polygramma, Pyrodinium bahamense,* etc.

The present controlling agent for algae has activity against various algae as mentioned above and inhibits algae from growth on glass surface of a water tank revise, algae from growth in a water-circulating apparatus, or marine animals and/o plants from adherence to a bottom of a ship when the agent is incorporated in paint. The present controlling agent is also superior in preventing red tide from blooming or outbreak which give heavy damage to a fish preserve of, for example, yellow tail, since the agent is remarkably active against dinoflagellates (Dinophyceae) which are planktons which cause red tide. The red tide is recently drawing public attention. Furthermore, the present controlling agent is able to serve as a treating agent for cultivation of layer such as a culturing net or a rope, since reversible retardation effect on cysts of laver readily disappears by dipping them again in sea water free from the present agent.

Higher fatty acid, the active ingredient of the present controlling agent, is used in the form of free acid or salts thereof such as alkali metal salts, alkaline earth metal salts, ammonium salts, organic quaternary ammonium salts or phosphonium salts. Alternatively, the acid or salts thereof may be used in the form of emulsifiable concentrate, powder, wettable powder, granule, soluble powder or solution in organic solvent such as ethanol. In the formulations above, various adjuvants such as a surfactant, a dispersant, a stabilizer etc. may be added.

An amount of the active ingredient in the composition is usually 1-99% by weight.

The effective concentration of the present controlling agent varies depending on the higher unsaturated fatty acid employed and varieties and growing density of algae to be applied to, but it is usually 0.01-1000 ppm, preferably 0.1-500 ppm, more preferably 0.1-100 ppm.

The emulsifiable concentrate, wettable powder or the like as above is distributed, after dilution with water, around or inside of a fish preserve when the present controlling agent is used for prevention of red tide. Alternatively, the active ingredient is coated on or impregnated in a net or a fence for a fish preserve. The net or fence may be made from a material in which the active ingredient is previously blended.

Experiment 1

Effect of the several unsaturated higher fatty acids on viability of *Heterosigma akashiwo.*

Test Organism

*Heterosigma akashiwo* was incubated in PES medium under 14 hr photoperiod (3000 lux) condition at 20° C. The effects of test compounds were examined on the plankton at exponential growth phase and the medium at the phase generally contained $7 \times 10^4$ cells/ml.

Preparation of Test Solution

The unsaturated higher fatty acid was accurately weighed and dissolved in benzene. An aliquot of the solution was transferred in a 10 ml volumetric flask. The benzene was removed in vacuo and the residue was dissolved in 0.2 ml of ethanol. A PES medium was added bit by bit to make a 10 ml solution.

Examination of Effects

Each of 1 ml of the plankton medium was transferred to the wells of a multi-dish at the cell number of $7 \times 10^4$. After good conditions of the plankton were confirmed under an inverted microscope, 1 ml of graded levels of the test solution was mixed. At specified intervals, morphological examination was conducted under the microscope, and effect concentration ($EC_{100}$) was defined as the minimum concentration at which all of the plankton tested were cytolyzed 30 min after introduction of a test material.

Results $EC_{100}$ values to the plankton are summarized in Table 1.

TABLE 1
Effects of the several unsaturated higher fatty acid on viability of *Heterosigma akashiwo*

| Compound | $EC_{100}$ (ppm) |
|---|---|
| 6Z, 9Z, 12Z, 15Z-octadecatetraenoic acid | 2.5 |
| arachidonic acid | 2.5 |
| γ-linolenic acid | 25 |
| linoleic acid | 25 |
| oleic acid | 70–80 |
| 5, 8, 11, 14, 17-eicosapentaenoic acid | 2.5 |

Experiment 2

Effect of 6Z, 9Z, 12Z, 15Z-octadecateraeonic acid (OTA) on viability of several plankton species.

The test system was the same as in Experiment 1, except test concentration of 5 and 25 ppm and test duration of 48 hr.

The summarized results are shown in Table 2.

TABLE 2
Effects of OTA on viability of several plankton species.

| Planktons | Effect* 5 ppm | 25 ppm |
|---|---|---|
| Dinophyceae | | |
| *Gymnodinium nagasakiense* | + | + |
| *Gymnodinium sanguineum* | + | + |
| *Heterocapsa triguetra* | + | + |
| *Prorocentrum micans* | + | + |
| Haptophyceae | | |
| *Cricosphaera roscoffensis* | ± | ± |
| Cryptophyceae | | |
| *Cryptomonas* sp. | + | + |
| Raphydophyceae | | |
| *Chattonella antiqua* | + | + |
| *Chattonella marina* | + | + |
| *Olisthodiscus luteus* | + | + |
| *Heterosigma akashiwo* | + | + |
| Euglenophyceae | | |
| *Eutreptia* sp. | + | + |
| Prasinophyceae | | |
| *Hafniomonas reticulata* | + | + |
| *Nephroselmis* sp. | + | + |
| *Pterosperma cristatum* | + | + |
| *Pyraminonas* sp. | + | + |
| *Tetraselmis cordiformis* | ± | ± |
| Chlorophyceae | | |
| *Chlamydomonas* sp. | + | + |
| *Oltmannsiella* sp. | + | + |
| Bacillariophyceae | | |
| *Chaetoceros debile* | + | + |
| *Skeletonema costatum* | + | + |
| *Stephanopyris palmeriana* | + | + |

*+: 100% cytolysis of planktons after 2 hr
±: No cytolysis but no movement
—: No effect

Reference Example 1

Acute toxicity of the several unsaturated higher fatty acids.

Test Organism

Killifish (*Oryzias latipes*) at adult stage were acclimated to laboratory conditions in dechlorinated water. Fish were withheld from food for 24 hr prior to the test.

Preparation of Test Solution

Graded levels of the compounds in 0.5 ml ethanol were added to glass vessels, and then mixed with 100 ml of dechlorinated fresh water. Five fish were introduced to the vessel and maintained for 48 hr at 25° C.

As a solvent control, 0.5% ethanol solution was used. Mortality and behavior were observed for 48 hr.

Results

The results are shown in Table 3.

TABLE 3
Acute toxicity of the unsaturated higher fatty acids to killfish

| Compound | Maximum no effect concentration (ppm) | $LC_{100}$ (ppm) |
|---|---|---|
| 6Z, 9Z, 12Z, 15Z-octadecatetraenoic acid | <20 ppm | >25 ppm |
| 5, 8, 11, 14, 17-eicosapentaenoic acid | <25 ppm | >30 ppm |
| Na salt of 5, 8, 11, 14, 17-eicosapentaenoic acid | <30 ppm | >50 ppm |
| γ-linolenic acid | <40 ppm | >50 ppm |
| sodium linolenate | <100 ppm | >150 ppm |

Reference Example 2

Isolation and identification of 6Z, 9Z, 12Z, 15Z-octadecatetraenoic acid from Mozuku (*Cladosiphon okamuranus*)

10 kg of salted Mozuku (*Cladosiphon okamuranus*) was extracted with methanol at room temperature for 2 weeks. A solid material was removed by filtration and the filtrate was concentrated in vacuo at a temperature below 30° C. 2% of ethanol was added to the concentrate and the precipitated solid material was removed by filtration. This process was repeated twice more to remove inorganic salts and sugars. The filtrate was concentrated in vacuo. To the concentrated syrup, was added 1l of water and the mixture was extracted three times with 1l of ether. The ether layers were combined and dried over anhydrous sodium sulfate. The ether layer was concentrated in vacuo to give 20 g of crude extract. The crude extract was chromatographed over a silica-gel column eluted with $CH_2Cl_2$/MeOH gradient solvent system. Each fractions were monitored by the bioassay against *Heterosigma akashiwo* described in Example 1. The algicidal activity was concentrated in the fraction eluted with $CH_2Cl_2$MeOH (95/5), and the fraction was evaporated in vacuo to give 5 g of an oily material.

Similar purifications with silica-gel column chromatography were repeated and the active component was purified finally by preparative medium pressure reversed phase column chromatography (Lobar RP-8, E. Merck, eluted with dioxane-$H_2O$ solvent system) twice to give 150 mg of 6Z, 9Z, 12Z, 15Z-octadecatetraenoic acid as an oily material. Since 6Z, 9Z, 12Z, 15Z-octadecatetraenoic acid was reported in Biochemistry Journal Vol 68, 695 (1958) by M. M. Matic et al, identification was made by comparison of IR, 'HNMR, $^{13}$CNMR and Mass spectrum of the corresponding methyl ester of the present compound against the reported data.

What is claimed is:

1. An algicidal composition which comprises as an active ingredient an algicidally effective amount of a higher fatty acid containing 16 to 22 carbon atoms having 4-5 carbon-carbon unsaturated bonds in molecule or its environmentally acceptable salt, and an inert carrier.

2. An algicidal composition according to claim 1, wherein the higher fatty acid or its environmentally acceptable salt is composed of that obtained by hydrolysis of fish oil.

3. An algicidal composition according to claim 1, wherein the higher fatty acid or its environmentally acceptable salt is 6, 9, 12, 15-octadecatetranoic acid, arachidonic acid or 5, 8, 11, 14, 17-eicosapentaenoic acid or their salt.

4. A method of controlling algae which comprises applying an algicidally effective amount of a higher fatty acid or its salt as claimed in claim 1 to algae selected from the group consisting of *Chattonella antiqua, Chattonella marina, Olisthodiscus luteus, Heterosigma akashiwo, Gymnodinium nagasakiense, Gymnodinium sanguineum* and *Gymnodinium breve.*

5. A method of controlling algae which comprises applying an algicidally effective amount of a higher fatty acid or its as claimed in claim 2 to algae selected from the group consisting of *Chattonella antiqua, Chattonella marina, Olisthodiscus luteus, Heterosigma akashiwo, Gymnodinium nagasakiense, Gymnodinium sanguineum* and *Gymnodinium breve.*

6. A method of controlling algae which comprises applying an algicidally effective amount of a higher fatty acid or its salt as claimed in claim 3 to algae selected from the group consisting of *Chattonella antiqua, Chattonella marina, Olisthodiscus luteus, Heterosigma akashiwo, Gymnodinium nagasakiense, Gymnodinium sanguineum* and *Gymnodinium breve.*

* * * * *